United States Patent [19]
Merz et al.

[11] 3,998,960
[45] Dec. 21, 1976

[54] PHARMACEUTICAL COMPOSITIONS CONTAINING A 2-(HETEROARYL-METHYL)-5,9β-DIALKYL-6,7-BENZOMORPHAN AND METHOD OF USE

[75] Inventors: Herbert Merz; Adolf Langbein; Klaus Stockhaus; Helmut Wick, all of Ingelheim am Rhein, Germany

[73] Assignee: Boehringer Ingelheim GmbH, Ingelheim am Rhein, Germany

[22] Filed: Oct. 30, 1975

[21] Appl. No.: 627,207

Related U.S. Application Data

[62] Division of Ser. No. 367,114, June 5, 1973, Pat. No. 3,931,194.

[30] Foreign Application Priority Data

June 19, 1972 Germany ............... 2229695

[52] U.S. Cl. .................... 424/275; 424/285
[51] Int. Cl.² ............... A61K 31/38; A61K 31/34
[58] Field of Search ............ 424/275, 285

Primary Examiner—Stanley J. Friedman
Attorney, Agent, or Firm—Hammond & Littell

[57] ABSTRACT

Pharmaceutical compositions containing as an active ingredient a compound of the formula

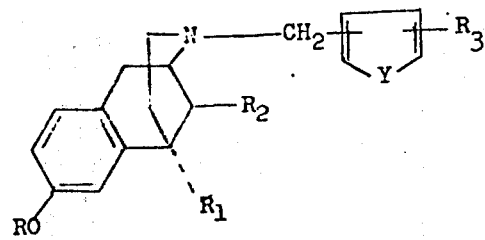

wherein
R is hydrogen, methyl or acetyl,
$R_1$ and $R_2$, which may be identical to or different from each other, are each alkyl of 1 to 3 carbon atoms,
$R_3$ is hydrogen or methyl, and
Y is oxygen or sulfur, or a non-toxic, pharmacologically acceptable acid addition salt thereof; and a method of using the same as analgesics, antitussives and opiate-antagonists.

12 Claims, No Drawings

PHARMACEUTICAL COMPOSITIONS CONTAINING A 2-(HETEROARYL-METHYL)-5,9β-DIALKYL-6,7-BENZOMORPHAN AND METHOD OF USE

This is a division of copending application Ser. No. 367,114 filed June 5, 1973, now U.S. Pat. No. 3,931,194 granted Jan. 6, 1976.

This invention relates to novel pharmaceutical compositions containing a 2-(heteroaryl-methyl)-5,9β-dialkyl-6,7-benzomorphan or a non-toxic acid addition salt thereof, as well as to a method of using the same as analgesics, antitussives and opiate-antagonists.

More particularly, the present invention relates to novel pharmaceutical compositions containing as an active ingredient a 2-(furylmethyl or thienylmethyl)-5,9β-di-lower alkyl-6,7-benzomorphan of the formula

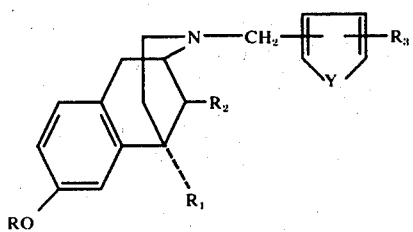

wherein
R is hydrogen, methyl or acetyl,
$R_1$ and $R_2$, which may be identical to or different from each other, are each alkyl of 1 to 3 carbon atoms,
$R_3$ is hydrogen or methyl, and
Y is oxygen or sulfur,
and non-toxic, pharmacologically acceptable acid addition salts thereof.

A preferred subgenus thereunder is constituted by pharmaceutical compositions containing a compound of the formula I wherein R is hydrogen and $R_1$, $R_2$, $R_3$ and Y have the meanings previously defined, or a non-toxic acid addition salt thereof.

In the compounds of the formula I the substituents $R_1$ and $R_2$ are in trans-configuration with respect to each other; benzomorphans of this configuration are designated as 5,9β-dialkyl-6,7-benzomorphans, as distinguished from the isomeric 5,9α-dialkyl compounds in which the substituents $R_1$ and $R_2$ are in cis-configuration with respect to each other.

The present invention embraces pharmaceutical compositions containing an optically inactive racemate or racemic mixture, or a pure optical antipode, of a compound of the formula I or a non-toxic acid addition salt thereof.

The compounds embraced by formula I may be prepared by a number of different methods, among which the following are most convenient and efficient:

METHOD A

By reacting a 5,9β-dialkyl-6,7-benzomorphan of the formula

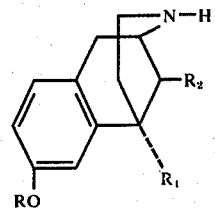

wherein R, $R_1$ and $R_2$ have the meanings previously defined, with a heteroarylmethyl derivative of the formula

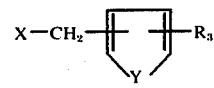

wherein
$R_3$ and Y have the meanings previously defined, and
X is a halogen, preferably chlorine, bromine or iodine, alkyl $-SO_2-O$, aryl$-SO_2-O-$ or trialkylammonium, preferably $(CH_3)3-N-$.

The reaction of the benzomorphan of the formula II is performed with the calculated amount, or a slight excess thereover, of the heteroarylmethyl derivative of the formula III, optionally in the presence of an acid-binding agent. Examples of suitable acid-binding agents are tertiary amines, such as triethylamine or N,N-dicyclohexyl ethylamine; alkali metal carbonates, such as sodium carbonate or potassium carbonate; alkali metal bicarbonates, preferably sodium bicarbonate; or alkali metal hydroxides or oxides. The reaction is advantageously carried out in an inert organic solvent medium, such as tetrahydrofuran, dioxane, methylene chloride, dimethylformamide, dimethylsulfoxide or a mixture of two or more of these, preferably mixtures of tetrahydrofuran and dimethylformamide. The reaction temperature may vary within wide limits, but a temperature between 0° C and the boiling point of the particular solvent medium which is used is preferred. After completion of the reaction, the reaction product is isolated and crystallized by conventional methods.

METHOD B

By reacting a 5,9β-dialkyl-6,7-benzomorphan of the formula II with formaldehyde and a furan of the formula

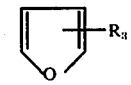

wherein $R_3$ has the meanings defined above.

The reaction is carried out in weakly acid solution, especially in an acetic acid solution, and preferably in aqueous 50% acetic acid. Other suitable solvents are water, lower alkanols, tetrahydrofuran, dioxane or mixtures of any two or more of these. The furan or thiophene of the formula IV is provided in the stoichiometric amount or in slight excess thereover, either dissolved or suspended in the solvent medium. The formaldehyde may be provided in the form of paraformaldehyde or preferably in the form of an aqueous solution in the calculated amount or in excess thereover. The reaction temperature may vary between −10° C and the boiling point of the particular solvent medium which is employed but the preferred temperature range is from 0° to 40° C. After completion of the reaction, the reaction product is isolated and crystallized by conventional methods.

METHOD C

By reacting a compound of the formula II with furaldehyde or thiophenaldehyde of the formula

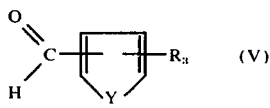

wherein $R_3$ and Y have the meanings previously defined, in the presence of catalytically activated hydrogen or formic acid.

In the reductive alkylation in the presence of catalytically activated hydrogen, the aldehyde V is used in the calculated quantity or in excess, preferably in an amount of up to 2 mols of aldehyde per mol of the compound of the formula II. The reaction is performed in a suitable solvent, such as an alcohol, preferably in methanol or ethanol. Various hydrogenation catalysts may be used, such as Raney nickel or similar catalysts, or pure metal catalysts, especially palladium or platinum contact catalysts. The latter may be used in finely dispersed form, in the free state or deposited on carriers, such as charcoal, barium sulfate, calcium carbonate, diatomateous earth or the like. If required, in order to avoid side-reactions, the activity of the catalysts may be attenuated, for instance by sulfidation. The quantity of catalyst is not critical and may therefore be varied in wide limits. The hydrogenation is advantageously effected while stirring or shaking at normal pressure or slightly elevated pressure, preferably at 1 to 3 atmospheres gauge. High reaction temperatures favor side-reactions; therefore, the reaction is preferably performed at room temperature or only slightly elevated temperature up to about 60° C. The reaction product is isolated and crystallized by conventional methods.

The reaction of a compound of the formula II with an aldeyde of the formula V in the presence of formic acid may be effected in aqueous solution, as well as in suitable organic solvents or mixtures of solvents. The aldehyde of the formula V is used in the calculated quantity or in excess thereover, preferably in an amount of up to 1.5 mols of aldehyde per mol of the compound of the formula II. The formic acid is advantageously provided in excess, preferably in an amount of 10 mols per mol of benzomorphan. The reaction is carried out at temperatures between 50° and 200° C, preferably between 80° and 150° C. The reaction product is isolated by conventional methods.

METHOD D

By reducing a 5,9β-dialkyl-6,7-benzomorphan carboxylic acid amide of the formula

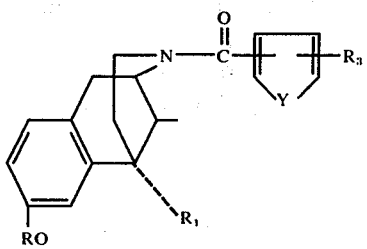

wherein R, $R_1$, $R_2$, $R_3$ and Y have the meanings previously defined.

Among the various suitable reduction methods, the reduction with a complex hydride, in particular with lithium aluminum hydride, is preferably used. Either the calculated quantity or, preferably, an excess of the hydride, advantageously up to double the calculated quantity, is provided. The reduction is advantageously performed in a suitable inert solvent or solvent mixture, such as ethers, but preferably in tetrahydrofuran. The reaction temperature is variable within wide limits. Temperatures between 0° C and the boiling point of the solvent or mixture of solvents are preferred.

If R in formula VI is acyl, the O-acyl group is split off simultaneously with the reduction of the carbonyl group, and in this case a compound of the formula I is obtained, wherein R is hydrogen. The reaction product is isolated and crystallized by conventional methods.

METHOD E

For the preparation of a compound of the formula I wherein R is hydrogen, by splitting off the protective substituent from a 2-(heteroaryl-methyl)-5.9β-dialkyl-6,7-benzomorphan of the formula

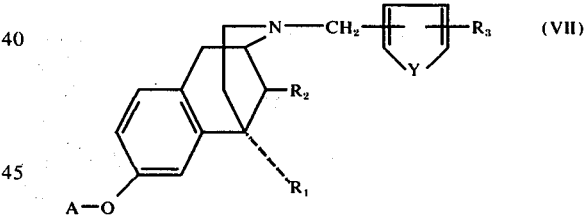

wherein $R_1$, $R_2$, $R_3$ and Y have the same meanings as in formula I, and A is a protective substituent for hydroxyl, such as alkyl, aralkyl or lower alkanoyl.

The removal of the protective substituent may be effected by hydrolysis or in special case also be hydrogenation; normally, hydrogenation will simultaneously remove the heteroarylmethyl substituent attached to the nitrogen atom as well.

METHOD F

For the preparation of a compound of the formula I wherein R is methyl or acetyl, by methylating or acetylating, respectively, a compound of the formula I wherein R is hydrogen.

The methylation is effected in conventional manner, that is, by reacting the 2′-hydroxy-5,9β-dialkyl-6,7-benzomorphan starting compound with a conventional methylating agent, such as diazomethane, a methyl ester of an inorganic acid, preferably dimethylsulfate, or phenyl trimethylammonium iodide.

The acetylation is effected with conventional acetylating agents, such as an acetyl halide, preferably acetyl chloride, or acetic acid anhydride.

The starting compounds required for methods A to D are, to a large extent, known compounds or may be prepared by known methods.

Methods A through F may be performed by starting from the racemic or the optically active benzomorphan derivatives, where, in the latter case, the corresponding optically active end products are formed. On the other hand, racemates or racemic mixtures of the end products of the formula I may be separated into their optical antipode components by conventional methods.

Several different methods for the preparation of the starting compounds of the formula II are described in the literature. A summary of the various methods may be found in N. B. Eddy et al, *Synthetic Analgesics*, part II B, Pergamon Press, Ltd., Oxford (1966).

For instance, a benzomorphan derivative of the formula II may be prepared by subjecting a compound of the formula

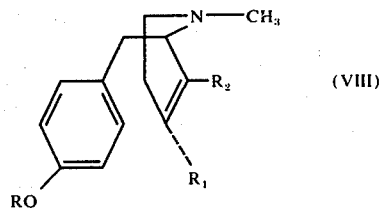

wherein R, $R_1$ and $R_2$ have the same meanings as in formula I, to a ring closure reaction, whereby primarily the α-isomer (in which $R_1$ and $R_2$ are in cis-configuration with respect to each other) is formed. The corresponding β-isomer may be isolated from the mother liquor of α-isomer separation.

A compound of the formula VI may be prepared by reacting a benzomorphan of the formula II with a carboxylic acid chloride of the formula

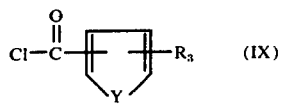

wherein $R_3$ and Y have the meanings previously defined.

Finally, a compound of the formula VII may be prepared by alkylating a compound of the formula

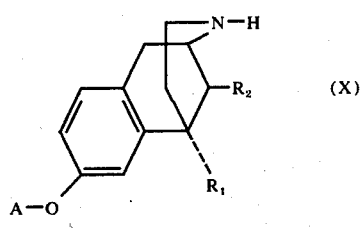

wherein $R_1$, $R_2$ and A have the meanings previously defined.

The heteroaryl derivatives of the formulas III, IV and V are known compounds which are readily available in commerce.

The compounds of the formula I are bases and therefore form acid addition salts with inorganic or organic acids. Examples of non-toxic, pharmacologically acceptable acid addition salts ar those formed with hydrochloric acid, hydrobromic acid, hydriodic acid, hydrofluoric acid, sulfuric acid, phosphoric acid, nitric acid, acetic acid, propionic acid, butyric acid, valeric acid, pivalic acid, caproic acid, oxalic acid, malonic acid, succinic acid, maleic acid, fumaric acid, lactic acid, tartaric acid citric acid, malic acid, benzoic acid, phthalic acid, cinnamic acid, salicylic acid, ascorbic acid, β-chlorotheophylline, methanesulfonic acid, ethanephosphonic acid or the like.

The following examples illustrate the preparation of various compounds of the formula I and their non-toxic acid addition salts.

EXAMPLE 1

2-Furfuryl-2'-hydroxy-5,9β-dimethyl-6,7-benzomorphan and its hydrochloride by method A A mixture consisting of 2.17 gm (0.01 mol) of 2'-hydroxy-5,9β-dimethyl-6,7-benzomorphan, 1.26 gm (0.15 mol) of sodium bicarbonate, 1.28 gm (0.011 mol) of furfuryl chloride, 15 ml of dimethylformamide and 25 ml of tetrahydrofuran was refluxed for 4 hours, accompanied by stirring. Thereafter, the reaction mixture was evaporated in vacuo, and the residue was shaken with a mixture consisting of 50 ml of chloroform and 25 ml of water. The aqueous phase was separated and again extracted with 10 ml of chloroform, and the combined chloroform solutions were washed with water, dried with sodium sulfate and evaporated in vacuo. The residue, the free base 2-furfuryl-2'-hydroxy-5,9β-dimethyl-6,7-benzomorphan, was dissolved in 20 ml of ethanol, the resulting solution was acidified with 4 ml of 2.5 Nethanolic hydrochloric acid, and then absolute ether was added thereto until the solution became cloudy. The mixture was allowed to stand in a refrigerator overnight, and the precipitate formed thereby was collected by vacuum filtration, washed with ethanol/ether (1:1) and then with ether, and finally dried first in the air and later at 80° C. 3.1 gm (91.5% of theory) of the hydrochlroide of the formula

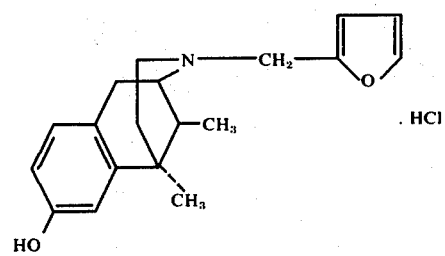

were obtained. It had a melting point of 249°–251° C which remained unchanged after recrystallization from ethanol/ether.

EXAMPLE 2

2-(3''-Thienyl-methyl)-2'-hydroxy-5,9β-dimethyl-6,7-benzomorphan and its hydrochloride by method A A mixture consisting of 1.09 gm (0.005 mol) of 2'-hydroxy-5,9β-dimethyl-6,7-benzomorphan, 0.63 gm of sodium bicarbonate, 1.0 gm of 3-(bromo-methyl)-thiophene, 10 ml of dimethylformamide and 20 ml of tetrahydrofuran was refluxed for four hours, accompanied by stirring. Thereafter, the reaction mixture was worked up as described in Example 1, yielding the free base, 2-(3''-thienyl-methyl)-2'-hydroxy-5,9β-dimethyl-6,7-benzomorphan, which was dissolved in 10 ml of absolute ethanol by addition of ethanolic hydrochloric acid thereto, and the resulting solution was admixed with ether until it became cloudy. The mixture was allowed to stand in a refrigerator overnight, and the crystalline substance which had separated out was collected by vacuum filtration, washed first with ethanol/ether (1:1) and then with ether, and dried initially in the air and then at 80° C. 1.1 gm (63% of theory) of the hydrochloride of the formula

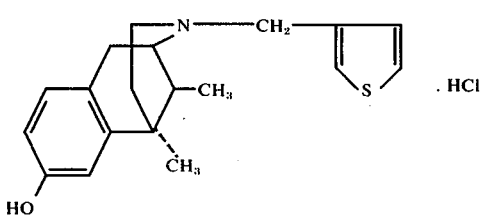

were obtained; it had a melting point of 286° C which remained unchanged after recrystallization from ethanol/ether.

EXAMPLE 3

2-(5''-Methyl-furfuryl)-2'-hydroxy-5,9β-dimethyl-6,7-benzomorphan and its methanesulfonate by method B A solution of 2.17 gm (0.01 mol) of 2'-hydroxy-5,9β-dimethyl-6,7-benzomorphan in 10 ml of aqueous 50% acetic acid was successively admixed with 1.1 gm of aqueous 30% formaldehyde and 1.0 gm of 2-methylfuran, accompanied by stirring, and the resulting mixture was stirred for 15 hours at room temperature. Thereafter, it was diluted with 50 ml of water and then, in the presence of ice, it was admixed with 15 ml of concentrated ammonia. The precipitate formed thereby was separated by extraction with three batches of chloroform of 50, 25 and 25 ml, respectively, and the combined chloroform extracts were washed with water, dried with sodium sulfate, and evaporated in vacuo. The residue, the free base 2-(5''-methyl-furfuryl)-2'-hydroxy-5,9β-dimethyl-6,7-benzomorphan, was dissolved in 50 ml of chloroform, and the resulting solution was chromatographed on 75 gm of aluminum oxide (activity III, neutral), using chloroform as the flow agent. The purified base was contained in the first three 250 ml-fractions of the eluate, which were combined and evaporated in vacuo. The residue was dissolved in 20 ml of ethanol by addition of 1.0 gm of methanesulfonic acid thereto, the resulting solution was admixed with absolute ether until it became cloudy, and the mixture was allowed to stand overnight in a refrigerator. Thereafter, the crystalline substance which had separated out was collected by vacuum filtration, washed first with ethanol/ether and then with ether, and dried at 80° C. 3.0 gm (73.5% of theory) of the methanesulfonate of the formula

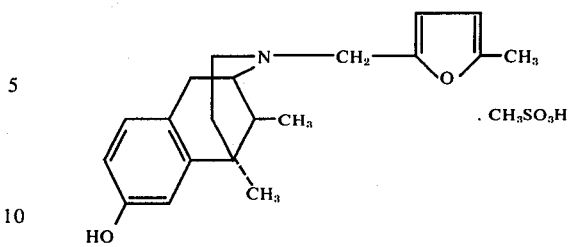

were obtained; it had a melting point of 217°–219° C. A sample recrystallized from methanol/ether had a melting point of 218°–220° C.

EXAMPLE 4

2-(2''-Thienyl-methyl)-2'-hydroxy-5,9β-dimethyl-6,7-benzomorphan and its hydrochloride by method C 2.17 gm (0.01 mol) of 2'-hydroxy-5,9β-dimethyl-6,7-benzomorphan and 2.5 gm of freshly distilled thiphene-2-aldehyde were dissolved in 120 ml of methanol, and the resulting solution was hydrogenated in the presence of about 1 gm of Raney nickel at 20° C under atmospheric pressure, accompanied by shaking. The hydrogenation was interrupted after five hours and, after addition of 1 gm of Raney nickel, it was resumed until a total of 350 ml of hydrogen had been absorbed, at which point the hydrogenation was terminated. The catalyst was removed by filtration through diatomaceous earth, the filtrate was evaporated in vacuo, the residue was dissolved in 15 ml of a mixture of chloroform/methanol/concentrated ammonia (volumetric ratio 90:10:0.5), and the solution was chromatographed on a silicagel column (300 gm of silicagel), using the above solvent mixture as the flow agent. The eluate was collected in 25 ml-fractions, and each of them was thin-layer-chromatographically tested for presence of the desired compound. The fractions containing the desired compound were combined and evaporated in vacuo, and the residue, 2-(2''-thienyl-methyl)-2'-hydroxy-5,9β-dimethyl-6,7-benzomorphan, was converted into its hydrochloride in the manner analogous to that described in Example 1. 0.6 gm (17% of theory) of the hydrochloride with a melting point of 252°–254° C were obtained.

EXAMPLE 5

2-(3''-Methyl-furfuryl)-2'-hydroxy-5,9β-dimethyl-6,7-benzomorphan and its methanesulfonate by method D 2.17 gm (0.01 mol) of 2'-hydroxy-5,9β-dimethyl-6,7-benzomorphan were dissolved in 70 ml of methanol by heating, and after the solution had cooled it was admixed at room temperature with a solution of 2.5 gm of potassium carbonate in 4 ml of water. A total of 1.6 gm (0.011 mol) of 3-methyl-furan-2-carboxylic acid chloride were now added to the solution in 0.4 gm-portions at 5 minute-intervals, and after the last portion had been added the reaction mixture was stirred for one hour at room temperature. Thereafter, the reaction solution was evaporated in vacuo, the residue was dissolved in 50 ml of chloroform, and the resulting solution was washed successively with 10 ml of water, 10 ml of 2 N hydrochloroic acid and again twice with water. The chloroform phase was then dried with sodium sulfate and evaporated in vacuo, and for removal of residual moisture the residue was dissolved in absolute benzene, and the resulting solution was again evaporated in vacuo.

The residue, 2-(3''-methyl-2''-furoyl)-2'-hydroxy-5,9β-dimethyl-6,7-benzomorphan, was dissolved in 40 ml of absolute tetrahydrofuran, and the resulting solution was added dropwise over a period of half an hour to a suspension of 0.76 gm (0.02 mol) of lithium aluminum hydride in 20 ml of absolute tetrahydrofuran on an ice bath, accompanied by stirring. The resulting reaction mixture was then allowed to warm to room temperature and was subsequently refluxed for two hours. Thereafter, the reaction mixture was cooled on an ice bath, and, while stirring, first 1.5 ml of water and then 75 ml of a saturated ammonium tartrate solution were added dropwise. The resulting mixture was vigorously stirred for one hour and was then allowed to stand in a separating funnel. The tetrahydrofuran (upper) phase was separated and evaporated in vacuo, and the aqueous phase was extracted three times with 25 ml of chloroform each. The residue of the evaporation of the tetrahydrofuran phase was dissolved in the combined chloroform extracts, and the resulting solution was washed with water, dried with sodium sulfate, and evaporated in vacuo. The residue, the free base 2-(3''-methyl-furfuryl)-2'-hydroxy-5,9β-dimethyl-6,7-benzomorphan, was converted into its methanesulfonate analogous to Example 3, yielding 3.5 gm (86.0% of theory) of the compound of the formula

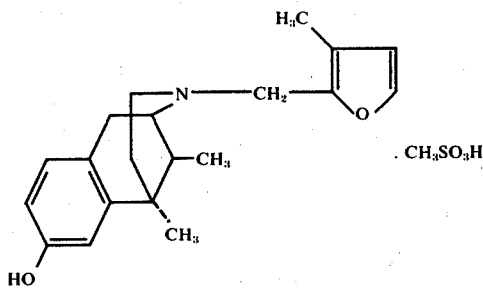

which had a melting point of 192°–194° C. A sample recrystallized from ethanol/ether had a melting point of 194°–195° C.

EXAMPLE 6

2-(3''-Furyl-methyl)-2'-hydroxy-5,9β-dimethyl-6,7-benzomorphan and its methanesulfonate by method D A solution of 2.9 gm (0.022 mol) of furan-3-carboxylic acid chloride in 10 ml of absolute methylene chloride was added dropwise over a period of about one hour to a suspension of 2.17 gm (0.01 mol) of 2'-hydroxy-5,9β-dimethyl-6,7-benzomorphan in a mixture of 22 ml of absolute methylene chloride and 4 ml of triethylamine, accompanied by stirring, and the resulting mixture was refluxed for four hours. Thereafter, it was allowed to cool and was then, in the presence of ice, washed twice with 10 ml of 2 N hydrochloric acid each and three times with water, dried with sodium sulfate and evaporated in vacuo. The residue was redissolved in absolute benzene, and the resulting solution was again evaporated in vacuo. The residue, 2-(3''-furoyl)-2'-(3'''-furoyloxy)-5,9β-dimethyl-6,7-benzomorphan, was dissolved in 40 ml of absolute tetrahydrofuran and reduced with 0.76 gm (0.02 mol) of lithium aluminum hydride to yield the free base 2-(3''-furyl-methyl)-2'-hydroxy-5,9β-dimethyl-6,7-benzomorphan which was converted into its methanesulfonate, in a manner analogous to that described in Example 5. 3.7 gm (91.0% of theory) of the compound of the formula

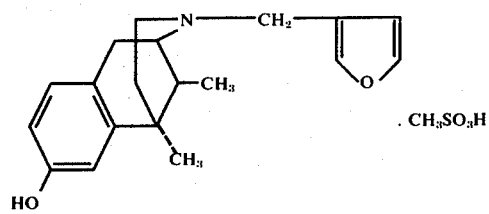

were obtained; it had a melting point of 217°–218° C which remained unchanged after recrystallization from ethanol/ether.

EXAMPLE 7

2-(2''-Methyl-3''-furylmethyl)-2'-hydroxy-5,9β-dimethyl-6,7-benzomorphan and its methanesulfonate by method E A mixture consisting of 0.5 gm of 2-(2''-methyl-3''-furylmethyl)-2'-acetoxy-5,9β-dimethyl-6,7-benzomorphan methanesulfonate, 15 ml of methanol and 10 ml of 2 N hydrochloric acid was refluxed for 30 minutes. Thereafter, the reaction solution was evaporated in vacuo, the residue was shaken with a mixture of 25 ml of 2 N ammonia and 50 ml of chloroform, the aqueous phase was separated and extracted twice with chloroform, and the chloroform extracts were combined, washed with water, dried with sodium sulfate and evaporated in vacuo. The residue, the free base 2-(2''-methyl-3''-furylmethyl)-2'-hydroxy-5,9β-dimethyl-6,7-benzomorphan, was converted into its methanesulfonate as described in Example 3, yielding 0.45 gm (about 100% of theory) of the compound of the formula

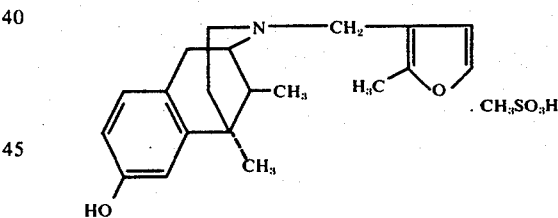

which had a melting point of 215°–216° C; after recrystallization from ethanol/ether it had a melting point of 218°–219° C.

EXAMPLE 8

2-Furfuryl-2'-acetoxy-5,9β-dimethyl-6,7-benzomorphan and its hydrochloride by method F A mixture consisting of 3.0 gm (0.01 mol) of 2-furfuryl-2'-hydroxy-5,9β-dimethyl-6,7-benzomorphan and 50 ml of acetic acid anhydride was heated for three hours on a boiling water bath. Thereafter, the unreacted excess acetic acid anhydride was substantially distilled off, and the residue was shaken with a mixture of 100 ml of ether and 50 ml of water in the presence of ice while adding sodium carbonate until the mixture remained alkaline. The ether phase was now separated, washed with water, dried with sodium sulfate and evaporated. The residue, the free base 2-furfuryl-2'-acetoxy-5,9β-dimethyl-6,7-benzomorphan, was converted into its hydrochloride in a manner analogous to that described in Example 1, but avoiding the addition of excess hydrochloric acid, yielding 2.2 gm (58.5% of theory) of the compound of the formula

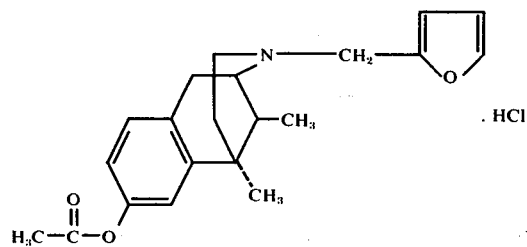

which had a melting point of 252°–253° C; it remained unchanged after recrystallization from ethanol/ether.

EXAMPLE 9

2-(3''-Furyl-methyl)-2'-methoxy-5,9β-dimethyl-6,7-benzomorphan and its methanesulfonate by method F 3.95 gm (0.01 mol) of 2-(3''-furyl-methyl)-2'-hydroxy-5,9β-dimethyl-6,7-benzomorphan methanesulfonate were shaken with a mixture of 50 ml of chloroform and 25 ml of 2 N ammonia, the chloroform phase was separated, and the aqueous phase was again extracted with chloroform. The combined chloroform phases were washed with water, dried with sodium sulfate and evaporated in vacuo. The residue, the free base 2-(3''-furylmethyl)-2'-hydroxy-5,9β-dimethyl-6,7-benzomorphan, was dissolved in 25 ml of tetrahydrofuran, the resulting solution was admixed with 0.018 mol of diazomethane (100 ml of an ethereal solution), and the mixture was allowed to stand for four days at room temperature. Thereafter, 5 ml of ethanolic 2 N hydrochloric acid were added to destroy the unreacted excess diazomethane, and the mixture was evaporated in vacuo. The residue was dissolved in 50 ml of chloroform, and the resulting solution was washed first with 20 ml of 2 N sodium hydroxide and then twice with water, dried with sodium sulfate and evaporated in vacuo. The residue, the free base 2-(3''-furylmethyl)-2'-methoxy-5,9β-dimethyl-6,7-benzomorphan, was dissolved in a small amount of ethanol by adding methane-sulfonic acid thereto, and precipitated as its methanesulfonate, in a manner analogous to that described in Example 3. 2.5 gm (61.5% of theory) of the compound of the formula

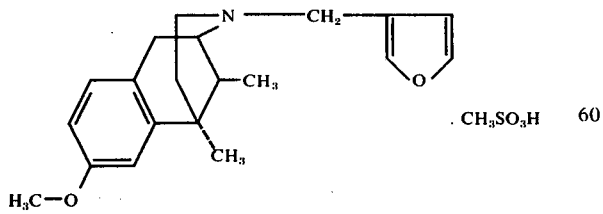

were obtained; it had a melting point of 187° C which did not change after recrystallization from ethanol/ether.

EXAMPLE 10

2-(2''-Methyl-3''-furylmethyl)-2'-methoxy-5,9β-dimethyl-6,7-benzomorphan and its hydrochloride by method F 4.1 gm (0.01 mol) of 2-(2''-methyl-3''-furylmethyl)-2'-hydroxy-5,9β-dimethyl-6,7-benzomorphan methanesulfonate were converted into the free base, in a manner analogous to that described in Example 9, and the base was dissolved in 3 ml of absolute methanol. The resulting solution was added to a mixture consisting of 1.9 gm (0.011 mol) of phenyl trimethyl ammonium chloride. 2.5 ml of methanol and 0.54 gm (0.01 mol) of sodium methylate, the sodium chloride precipitated thereby was separated by vacuum filtration, and the filtrate was evaporated. The residue was dissolved in 2 ml of dimethylformamide, and the resulting solution was again evaporated to remove residual methanol. The residue was again dissolved in 10 ml of dimethylformamide, the solution was refluxed for 2 hours and then evaporated in vacuo, and the residue was extracted by shaking with a mixture of 50 ml of chloroform and 20 ml of 2 N sodium hydroxide. The chloroform phase was separated, washed twice with water, dried with sodium sulfate and evaporated in vacuo. The residue, the free base 2-(2''-methyl-3''-furylmethyl)-2'-methoxy-5,9β-dimethyl-6,7-benzomorphan, was dissolved in a little ethanol and, by acidification with ethanolic hydrochloric acid and addition of ether, precipitated as its hydrochloride which had a melting point of 280°–281° C. The yield was 1.7 gm (47% of theory).

EXAMPLE 11

Using a procedure analogous to that described in Example 1, 2-furfuryl-2'-methoxy-5,9β-dimethyl-6,7-benzomorphan and its methanesulfonate, m.p. 164° C, were prepared from 2'-methoxy-5,9β-dimethyl-6,7-benzomorphan and furfuryl chloride. The yield of methanesulfonate was 89.5% of theory.

EXAMPLE 12

Using a procedure analogous to that described in Example 5, 2-(3''-methyl-furfuryl)-2'-methoxy-5,9β-dimethyl-6,7-benzomorphan and its hydrochloride, m.p. 195°–196° C, were prepared from 2'-methoxy-5,9β-dimethyl-6,7-benzomorphan and 3-methyl-furan-2-carboxylic acid chloride. The yield of hydrochloride was 77.5% of theory.

EXAMPLE 13

Using a procedure analogous to that described in Example 8, 2-(3''-furylmethyl)-2'-acetoxy-5,9β-dimethyl-6,7-benzomorphan and its hydrochloride, m.p. 276°–278° C, were prepared from 2-(3''-furylmethyl)-2'-hydroxy-5,9β-dimethyl-6,7-benzomorphan and acetic acid anhydride. The yield of hydrochloride was 51.5% of theory.

EXAMPLE 14

Using a procedure analogous to that described in Example 8, 2-(3''-methyl-furfuryl)-2'-acetoxy-5,9β-dimethyl-6,7-benzomorphan and its hydrochloride, m.p. 232° C, were prepared from 2-(3''-methyl-furfuryl)-2'-hydroxy-5,9β-dimethyl-6,7-benzomorphan and acetic acid anhydride. The yield of hydrochloride was 62.0% of theory.

EXAMPLE 15

Using a procedure analogous to that described in Example 8, 2-(2''-methyl-3''-furylmethyl)-2'-acetoxy-5,9β-dimethyl-6,7-benzomorphan and its hydrochloride, m.p. 282° C, were prepared from 2-(2''-methyl-3''-furylmethyl)-2'-hydroxy-5,9β-dimethyl-6,7-benzomorphan and acetic acid anhydride. The yield of hydrochloride was 56.5% of theory.

EXAMPLE 16

Using a procedure analogous to that described in Example 5, 2-(5''-methyl-3''-furylmethyl)-2'-hydroxy-5,9β-dimethyl-6,7-benzomorphan and its methanesulfonate, m.p. 261–263° C, were prepared from 2'-hydroxy-5,9β-dimethyl-6,7-benzomorphan and 5-methyl-furan-3-carboxylic acid chloride. The yield of methanesulfonate was 95.5% of theory.

EXAMPLE 17

Using a procedure analogous to that described in Example 5, 2-(4''-methyl-furfuryl)-2'-methoxy-5,9β-dimethyl-6,7-benzomorphan and its hydrochloride, m.p. 237° C, were prepared from 2'-methoxy-5,9β-dimethyl-6,7-benzomorphan and 4-methyl-furan-2-carboxylic acid chloride. The yield of hydrochloride was 37.0% of theory.

EXAMPLE 18

Using a procedure analogous to that described in Example 5, 2-furfuryl-2'-hydroxy-5,9β-diethyl-6,7-benzomorphan of the formula

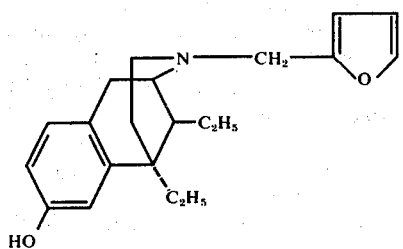

and its methanesulfonate, m.p. 190°–192° C, were prepared from 2'-hydroxy-5,9β-diethyl-6,7-benzomorphan and furan-2-carboxylic acid chloride. The yield of methanesulfonate was 66.0% of theory.

EXAMPLE 19

Using a procedure analogous to that described in Example 5, 2-(3''-methyl-furfuryl)-2'-hydroxy-5,9β-dimethyl-6,7-benzomorphan and its methanesulfonate, m.p. 197°–199° C, were prepared from 2'-hydroxy-5,9β-diethyl-6,7-benzomorphan and 3-methyl-furan-2-carboxylic acid chloride. The yield of methanesulfonate was 75.0% of theory.

EXAMPLE 20

Using a procedure analogous to that described in Example 5, 2-(3''-furylmethyl)-2'-hydroxy-5,9β-diethyl-6,7-benzomorphan and its methanesulfonate, m.p. 204°–205° C, were prepared from 2'-hydroxy-5,9β-diethyl-6,7-benzomorphan and furan-3-carboxylic acid chloride. The yield of methanesulfonate was 63.0% of theory.

EXAMPLE 21

Using a procedure analogous to that described in Example 5, 2-(2''-methyl-3''-furylmethyl)-2'-hydroxy-5,9β-diethyl-6,7-benzomorphan and its methanesulfonate, m.p. 244°–246° C, were prepared from 2'-hydroxy-5,9β-diethyl-6,7-benzomorphan and 2-methyl-furan-3-carboxylic acid chloride. The yield of methanesulfonate was 86.0% of theory.

EXAMPLE 22

Using a procedure analogous to that described in Example 5, 2-furfuryl-2'-hydroxy-5-ethyl-9β-methyl-6,7-benzomorphan of the formula

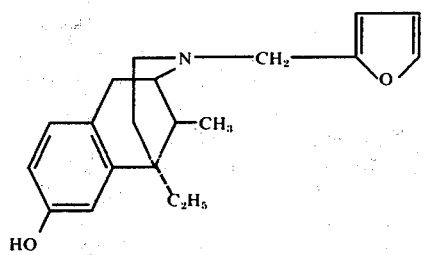

and its methanesulfonate, m.p. 228°–231° C, were prepared from 2'-hydroxy-5-ethyl-9β-methyl-6,7-benzomorphan and furan-2-carboxylic acid chloride. The yield of methanesulfonate was 67.5% of theory.

EXAMPLE 23

Using a procedure analogous to that described in Example 5, 2-(3''-furylmethyl)-2'-hydroxy-5-ethyl-9β-methyl-6,7-benzomorphan and its methanesulfonate, m.p. 221°–224° C, were prepared from 2'-hydroxy-5-ethyl-9β-methyl-6,7-benzomorphan and furan-3-carboxylic acid chloride. The yield of methanesulfonate was 55.0% of theory.

EXAMPLE 24

Using a procedure analogous to that described in Example 5, 2-(3''-methyl-furfuryl)-2'-hydroxy-5-ethyl-9β-methyl-6,7-benzomorphan and its methanesulfonate, m.p. 194°–196° C, were prepared from 2'-hydroxy-5-ethyl-9β-methyl-6,7-benzomorphan and 3-methyl-furan-2-carboxylic acid chloride. The yield of methanesulfonate was 61.5% of theory.

EXAMPLE 25

Using a procedure analogous to that described in Example 5, 2-(2''-methyl-3''-furylmethyl)-2'-hydroxy-5-ethyl-9β-methyl-6,7-benzomorphan and its methanesulfonate, m.p. 183°–185° C, were prepared from 2'-hydroxy-5-ethyl-9β-methyl-6,7-benzomorphan and 2-methyl-furan-3-carboxylic acid chloride. The yield of methanesulfonate was 61.5% of theory.

EXAMPLE 26

Using a procedure analogous to that described in Example 5, 2-furfuyl-2'-hydroxy-5-methyl-9β-ethyl-6,7-benzomorphan of the formula

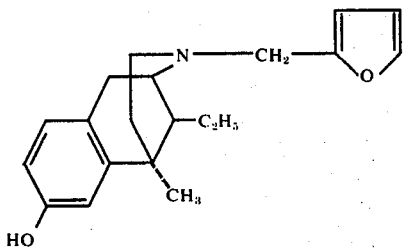

and its methanesulfonate, m.p. 190° C, were prepared from 2'-hydroxy-5-methyl-9β-ethyl-6,7-benzomorphan and furan-2-carboxylic acid chloride. The yield of methanesulfonate was 45.0% of theory.

EXAMPLE 27

Using a procedure analogous to that described in Example 5, 2-(3''-furylmethyl)-2'-hydroxy-5-methyl-9β-ethyl-6,7-benzomorphan and ite methanesulfonate, m.p. 215° C, were prepared from 2'-hydroxy-5-methyl-9β-ethyl-6,7-benzomorphan and furan-3-carboxylic acid chloride. The yield of methanesulfonate was 46.5% of theory.

EXAMPLE 28

Using a procedure analogous to that described in Example 5, 2-(3''-methyl-furfuryl)-2'-hydroxy-5-methyl-9β-ethyl-6,7-benzomorphan and its methanesulfonate, m.p. 228° C, were prepared from 2'-hydroxy-5-methyl-9β-ethyl-6,7-benzomorphan and 3-methyl-furan-2-carboxylic acid chloride. The yield of methanesulfonate was 51.5% of theory.

EXAMPLE 29

Using a procedure analogous to that described in Example 5, 2-(2''-methyl-3''-furylmethyl)-2'-hydroxy-5-methyl-9β-ethyl-6,7-benzomorphan and its methanesulfonate, m.p. 248° C, were prepared from 2'-hydroxy-5-methyl-9β-ethyl-6,7-benzomorphan and 2-methyl-furan-3-carboxylic acid chloride. The yield of methanesulfonate was 54.0% of theory.

EXAMPLE 30

Using a procedure analogous to that described in Example 1, 2-(2''-thienyl-methyl)-2'-hydroxy-5-methyl-9β-ethyl-6,7-benzomorphan and its methanesulfonate, m.p. 230° C, were prepared from 2'-hydroxy-5-methyl-9β-ethyl-6,7-benzomorphan and 2-(chloromethyl)-thiophene. The yield of methanesulfonate was 44.0% of theory.

EXAMPLE 31

Using a procedure analogous to that described in Example 1, (−)-2-(2''-methyl-3''-furylmethyl)-2'-hydroxy-5,9β-dimethyl-6,7-benzomorphan and its hydrochloride, m.p. 288°–290° C, were prepared from (−)-2'-hydroxy-5,9β-dimethyl-6,7-benzomorphan and 2-methyl-3-chloromethyl-furan. The yield of hydrochloride was 85.0% of theory.

EXAMPLE 32

Using a procedure analogous to that described in Example 1, (+)-2-(2''-methyl-3''-furylmethyl)-2'-hydroxy-5,9β-dimethyl-6,7-benzomorphan and its hydrochloride, m.p. 288°–290° C, were prepared from (+)-2'-hydroxy-5,9β-dimethyl-6,7-benzomorphan and 2-methyl-3-chloromethyl-furan. The yield of hydrochloride was 81.0% of theory.

The compounds embraced by formula I and their non-toxic, pharmacologically acceptable acid addition salts, have useful pharmacodynamic properties. More particularly, the furan compounds exhibit non-narcotic analgesic, antagonistic and antitussive activities in warm-blooded animals, such as mice and rats, whereas in the thiophene derivatives the opiate-antagonistic activity is predominant. The compounds of the formula I differ from the corresponding α-isomers mainly in their significantly lower toxicity.

All of the compounds of the formula I and their non-toxic acid addition salts proved to be ineffective as analgesics in the Haffner test for analgesia [Deutsche Medizinische Wochenschrift 55, 731 (1929)] on mice and rats.

On the other hand, the compounds and especially the 3-methyl-2-furylmethyl-substituted derivatives, exhibit a distinct, dose-dependent analgesic activity in more sensitive pharmacological tests for analgesia, such as the hot-plate test [J.Pharmacol.Exp.Therap. 80, 300 (1944)] or the writhing test [J.Pharmacol.Exp. Therap. 154, 319 (1966)].

In accordance with presently prevailing teachings [Adv. Chem. Soc. 49, 162–169 (1964)], inactivity in the Haffner test is indicative of non-narcotic properties, while activity in the hot-plate test and/or writhing test proves analgesic properties.

For pharmaceutical purposes the compounds of the formula I or their non-toxic acid addition salts are administered to warm-blooded animals perorally, enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective analgesic and antiussive dosage unit of the compounds of the formula I and their non-toxic acid addition salts is from 0.166 to 5.0 mgm/kg body weight, preferably 0.83 to 3.4 mgm/kg body weight.

The following examples illustrate a few pharmaceutical dosage unit compositions comprising a compound of the formula I or a non-toxic acid addition salt as an active ingredient and represent the best modes contemplated of putting the invention into practical use. The parts are parts by weight unless otherwise specified.

EXAMPLE 33

Tablets

The tablet composition is compounded from the following ingredients:

| | |
|---|---|
| 2-(3''-furylmethyl)-2'-hydroxy-5,9β-dimethyl-6,7-benzomorphan methanesulfonate | 50.0 parts |
| Lactose | 95.0 parts |
| Corn starch | 45.0 parts |
| Colloidal silicic acid | 2.0 parts |
| Soluble starch | 5.0 parts |
| Magnesium stearate | 3.0 parts |
| Total | 200.0 parts |

PREPARATION

The benzomorphan compound is intimately admixed with the lactose and the corn starch, the mixture is moistened with an aqueous 10% solution of the soluble starch, the moist mass is forced through a 1 mm-mesh screen, the resulting granulate is dried at 40° C, the dry granulate is admixed with the colloidal silicic acid, and the composition is compressed into 200 mgm-tablets in a conventional tablet making machine. Each tablet contains 50 mgm of the benzomorphan compound and is an oral dosage unit composition with effective analgesic, antitussive and opiate-antagonistic actions.

EXAMPLE 34

Coated pills

The pill core composition is compounded from the following ingredients:

| | |
|---|---|
| 2-(3''-Furylmethyl)-2'-hydroxy-5,9$\beta$-dimethyl-6,7-benzomorphan hydrochloride | 75.0 parts |
| Lactose | 100.0 parts |
| Corn starch | 65.0 parts |
| Colloidal silicic acid | 2.0 parts |
| Soluble starch | 5.0 parts |
| Magnesium stearate | 3.0 parts |
| Total | 250.0 parts |

PREPARATION

The ingredients are compounded in the same manner as in Example 33, and the composition is compressed into 250 mgm-pill cores which are subsequently coated with a thin shell consisting essentially of a mixture of sugar, talcum and gum arabic and finally polished with beeswax. Each coated pill contains 75 mgm of the benzomorphan compound and is an oral dosage unit composition with effective analgesic, antitussive and opiate-antagonistic activities.

EXAMPLE 35

Suppositories

The suppository composition is compounded from the following ingredients:

| | |
|---|---|
| 2-(3''-Methyl-furfuryl)-2'-hydroxy-5,9$\beta$-dimethyl-6,7-benzomorphane methanesulfonate | 50.0 parts |
| Lactose | 200.0 parts |
| Suppository base (e.g. cocoa butter) | 1450.0 parts |
| Total | 1700.0 parts |

PREPARATION

The benzomorphan compound is intimately admixed with the lactose, and the mixture is blended with the aid of an immersion homogenizer into the suppository base which had previously been melted and cooled to about 40° C. 1700 mgm-portions of the composition are poured into cooled suppository molds and allowed to harden therein. Each suppository contains 50 mgm of the benzomorphan compound and is a rectal dosage unit composition with effective analgesic, antitussive and opiate-antagonistic actions.

EXAMPLE 36

Hypodermic solution

The solution is compounded from the following ingredients:

| | |
|---|---|
| 2-(3''-Methyl-furfuryl)-2'-hydroxy-5,9$\beta$-dimethyl-6,7-benzomorphan methanesulfonate | 75.0 parts |
| Sodium chloride | 5.0 parts |
| Double-distilled water q.s.ad | 2000.0 parts by vol. |

PREPARATION

The benzomorphan compound and the sodium chloride are dissolved in the double-distilled water, the solution is filtered until free from suspended particles, and the filtrate is filled under aseptic conditions into 2 cc-ampules which are subsequently sterilized and sealed. Each ampule contains 75 mgm of the benzomorphan compound, and its contents are an injectable dosage unit composition with effective analgesic, antitussive and opiate-antagonistic actions.

EXAMPLE 37

Drop solution

The solution is compounded from the following ingredients:

| | |
|---|---|
| 2-(3''-Methyl-furfuryl)-2'-hydroxy-5,9$\beta$-dimethyl-6,7-benzomorphan methanesulfonate | 0.70 parts |
| Methyl p-hydroxy-benzoate | 0.70 parts |
| Propyl p-hydroxy-benzoate | 0.03 parts |
| Demineralized water q.s.ad | 100.0 parts by vol. |

PREPARATION

The benzomorphan compound and the p-hydroxybenzoates are dissolved in the demineralized water, the solution is filtered, and the filtrate is filled into 100 ml-bottles. 10 ml of the solution contain 70 mgm of the benzomorphan compound and are an oral dosage unit composition with effective analgesic, antitussive and opiate-antagonistic actions.

Analogous results are obtained when any one of the other optically active or inactive compounds embraced by formula I or a non-toxic acid addition salt thereof is substituted for the particular benzomorphan in Examples 33 through 37. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An analgesic, antitussive or opiate-antagonistic pharmaceutical dosage unit composition consisting essentially of an inert pharmaceutical carrier and an effective analgesic, antitussive or opiate-antagonistic amount of a compound of the formula

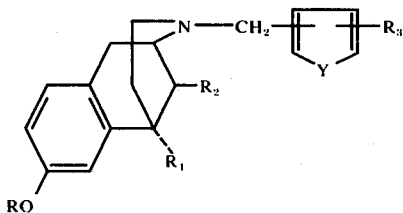

wherein
R is hydrogen, methyl or acetyl,
$R_1$ and $R_2$ are each alkyl of 1 to 3 carbon atoms,
$R_3$ is hydrogen or methyl, and
Y is oxygen or sulfur,
or a non-toxic, pharmacologically acceptable acid addition salt thereof.

2. A composition of claim 1,
where
R is hydrogen, methyl or acetyl,
$R_1$ and $R_2$ are each methyl or ethyl,
$R_3$ is hydrogen or methyl, and
Y is oxygen.

3. A composition of claim 1,
where
R is hydrogen,
$R_1$ and $R_2$ are each methyl or ethyl,
$R_3$ is hydrogen or methyl, and
Y is oxygen.

4. A composition of claim 1,
where
R is hydrogen,
$R_1$ and $R_2$ are methyl,
$R_3$ is hydrogen, and
Y is sulfur.

5. A composition of claim 1, where said compound is 2-(3''-methyl-furfuryl)-2'-hydroxy-5,9β-dimethyl-6,7-benzomorphan or a non-toxic pharmacologically acceptable acid addition salt thereof.

6. A composition of claim 1, where said compound is 2-(3''-furyl-methyl)-2'-hydroxy-5,9β-dimethyl-6,7-benzomorphan or a non-toxic pharmacologically acceptable acid addition salt thereof.

7. The method of raising the pain threshold, suppressing the cough reflex or counteracting the physiological effects of an opiate in a warm-blooded animal, which comprises administering to said animal an effective analgesic, antitussive or opiate-antagonistic amount of a compound of the formula

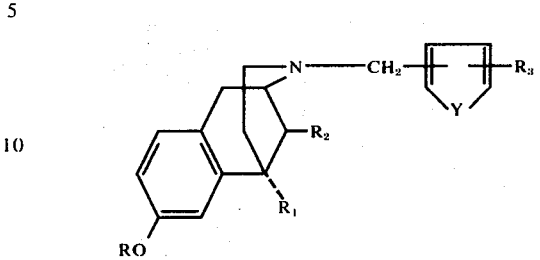

wherein
R is hydrogen, methyl or acetyl,
$R_1$ and $R_2$ are each alkyl of 1 to 3 carbon atoms,
$R_3$ is hydrogen or methyl, and
Y is oxygen or sulfur,
or a non-toxic, pharmacologically acceptable acid addition salt thereof.

8. The method of claim 7,
where
R is hydrogen, methyl or acetyl,
$R_1$ and $R_2$ are each methyl or ethyl,
$R_3$ is hydrogen or methyl, and
Y is oxygen.

9. The method of claim 7,
where
R is hydrogen,
$R_1$ and $R_2$ are each methyl or ethyl,
$R_3$ is hydrogen or methyl, and
Y is oxygen.

10. The method of claim 7,
where
R is hydrogen,
$R_1$ and $R_2$ are methyl,
$R_3$ is hydrogen, and
Y is sulfur.

11. The method of claim 7, where said compound is 2-(3''-methyl-furfuryl)-2'-hydroxy-5,9β-dimethyl-6,7-benzomorphan or a non-toxic, pharmacologically acid addition salt thereof.

12. The method of claim 7, where said compound is 2-(3''-furyl-methyl)-2''-hydroxy-5,9β-dimethyl-6,7-benzomorphan or a non-toxic, pharmacologically acceptable acid addition salt thereof.

* * * * *